United States Patent [19]

Hockfield et al.

[11] Patent Number: 5,635,370
[45] Date of Patent: Jun. 3, 1997

[54] DNA ENCODING BEHAB, A BRAIN HYALURONAN-BINDING PROTEIN, AND RECOMBINANT EXPRESSION SYSTEMS FOR PRODUCTION OF BEHAB POLYPEPTIDES

[75] Inventors: Susan Hockfield, North Haven; Diane M. Jaworski, New Haven, both of Conn.

[73] Assignee: Yale University

[21] Appl. No.: 225,477

[22] Filed: Apr. 8, 1994

[51] Int. Cl.$^6$ .............................. C12N 15/12; C12N 5/10; C07K 14/47
[52] U.S. Cl. .................. 435/69.1; 536/23.5; 536/24.31; 435/320.1; 435/325; 435/252.3; 435/254.11
[58] Field of Search .................. 536/23.5, 24.31; 435/320.1, 240.2, 252.3, 254.11, 69.1

[56] References Cited

PUBLICATIONS

Stavrou, D., et al. (1989) *Anticanc. Res.* 9: 1489–96.
Yamada, H., et al. (01 Apr. 1994) *J. Biol. Chem.* 269: 10119–26.
Seidenbecher, I. C., et al. (27 Jun. 1994) GenBank database record, Acc. No. X79881.

Adams, M. D. et al., (30 Jun. 1993) GenBank database record, Acc. No. T04913.

Adams, M. D. et al., (1993) *Nature Genetics* 4: 256–67.

Jaworski, D. M., et al. (1995) *J. Neurosci.* 1352–62.

*Primary Examiner*—David L. Fitzgerald
*Attorney, Agent, or Firm*—Mary M. Krinsky; St. Onge Steward Johnston & Reens

[57] ABSTRACT

A gene encoding mammalian brain enriched hyaluronan binding (BEHAB) protein is isolated and characterized from brain tissue and found to have a high degree of sequence homology to members of the proteoglycan tandem repeat family of hyaluronan binding proteins. Unlike other members of the family, however, the expression of the gene is restricted to the central nervous system. BEHAB is expressed in markedly increased levels in human glioma tissue, so that the polypeptide can be used as a marker for diagnostic purposes.

24 Claims, 2 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1520 bases
        ( B ) TYPE: nucleic acid
        ( C ) STRANDEDNESS: double
        ( D ) TOPOLOGY: linear ( i i ) MOLECULE TYPE:
        ( A ) DESCRIPTION: DNA encoding a protein ( v ) FRAGMENT TYPE: entire sequence ( v i ) IMMEDIATE SOURCE: rat brain ( i x ) FEATURE:
        ( A ) NAME/KEY: rat BEHAB ( x i ) SEQUENCE DESCRIPTION: SEQ ID NO:1:

```
         CG AGACCCGCGC AGAGAAGGGA GCGGGTCCCG TGACCGCGCA         4 2

GAGCCCCCCA CGCGGCCAAA GGCCGGGGAC GCGGGGAAGG CGGGGCGCGT         9 2

GGGAAGAAAC CCCCTTTTGT GCGGCTCCCG GCGAGCTGGC GCCCCCGTCT       1 4 2
```

```
GCGTCCCGCG CGCCCGGCCC TGCTCGCGCC CGCGCATTGC CGCAGTCTCG            192

GCTGCGTGCG GGACGCGGTG TGTGGAGGGG ACCTCACAAG TTCTTCCAAG            242

TTTGCAGC ATG ATC CCA TTG CTT CTG TCC CTG CTG GCA GCT CTG          286
        Met Ile Pro Leu Leu Leu Ser Leu Leu Ala Ala Leu
                         5                    10

GTC CTG ACC CAA GCC CCT GCA GCC CTC GCT GAT GAC CTG AAA            328
Val Leu Thr Gln Ala Pro Ala Ala Leu Ala Asp Asp Leu Lys
         15              20              25

GAA GAC AGC TCA GAG GAT CGA GCC TTT CGG GTG CGC ATC GGT            370
Glu Asp Ser Ser Glu Asp Arg Ala Phe Arg Val Arg Ile Gly
             30              35                      40

GCC GCG CAG CTG CGG GGT GTG CTG GGC GGT TGG GTG GCC ATC            412
Ala Ala Gln Leu Arg Gly Val Leu Gly Gly Trp Val Ala Ile
                 45              50

CCA TGC CAC GTC CAC CAC CTG AGG CCG CCG CCC AGC CGC CGG            454
Pro Cys His Val His His Leu Arg Pro Pro Pro Ser Arg Arg
55              60              65

GCC GCG CCG GGC TTT CCC CGA GTC AAA TGG ACC TTC CTG TCC            496
Ala Ala Pro Gly Phe Pro Arg Val Lys Trp Thr Phe Leu Ser
         70              75              80

GGG GAC CGG GAG GTG GAG GTG CTG GTG GCG CGC GGG CTG CGC            538
Gly Asp Arg Glu Val Glu Val Leu Val Ala Arg Gly Leu Arg
             85              90                      95

GTC AAG GTA AAC GAA GCC TAT CGG TTC CGC GTG GCG CTG CCT            580
Val Lys Val Asn Glu Ala Tyr Arg Phe Arg Val Ala Leu Pro
                 100             105                 110

GCC TAC CCC GCA TCG CTC ACA GAT GTG TCT TTA GTA TTG AGC            622
Ala Tyr Pro Ala Ser Leu Thr Asp Val Ser Leu Val Leu Ser
                 115             120

GAA CTG CGG CCC AAT GAT TCC GGG GTC TAT CGC TGC GAG GTC            664
Glu Leu Arg Pro Asn Asp Ser Gly Val Tyr Arg Cys Glu Val
125             130             135

CAG CAC GGT ATC GAC GAC AGC AGT GAT GCT GTG GAA GTC AAG            706
Gln His Gly Ile Asp Asp Ser Ser Asp Ala Val Glu Val Lys
    140             145             150

GTC AAA GGG GTC GTC TTC CTC TAC CGA GAG GGC TCT GCC CGC            748
Val Lys Gly Val Val Phe Leu Tyr Arg Glu Gly Ser Ala Arg
        155             160             165

TAT GCT TTC TCC TTC GCT GGA GCC CAG GAA GCC TGT GCT CGC            790
Tyr Ala Phe Ser Phe Ala Gly Ala Gln Glu Ala Cys Ala Arg
            170             175                 180

ATC GGA GCC CGA ATT GCC ACC CCT GAG CAG CTG TAT GCT GCC            832
Ile Gly Ala Arg Ile Ala Thr Pro Glu Gln Leu Tyr Ala Ala
                185             190

TAC CTC GGC GGC TAT GAA CAG TGT GAT GCT GGC TGG CTG TCC            874
Tyr Leu Gly Gly Tyr Glu Gln Cys Asp Ala Gly Trp Leu Ser
195             200             205

GAC CAA ACC GTG AGG TAC CCC ATC CAG AAC CCA CGA GAA GCC            916
Asp Gln Thr Val Arg Tyr Pro Ile Gln Asn Pro Arg Glu Ala
    210             215             220

TGT TAT GGA GAC ATG GAT GGC TAC CCT GGA GTG CGG AAT TAC            958
Cys Tyr Gly Asp Met Asp Gly Tyr Pro Gly Val Arg Asn Tyr
        225             230             235

GGA GTG GTG GGT CCT GAT GAT CTC TAC GAT GTC TAC TGT TAT           1000
Gly Val Val Gly Pro Asp Asp Leu Tyr Asp Val Tyr Cys Tyr
            240             245             250

GCC GAA GAC CTA AAT GGA GAA CTG TTC CTA GGT GCC CCT CCC           1042
Ala Glu Asp Leu Asn Gly Glu Leu Phe Leu Gly Ala Pro Pro
                255             260
```

```
GGC AAG CTG ACG TGG GAG GAG GCT CGG GAC TAC TGT CTG GAA        1084
Gly Lys Leu Thr Trp Glu Glu Ala Arg Asp Tyr Cys Leu Glu
265             270             275

CGC GGT GCT CAG ATC GCT AGC ACG GGC CAG CTA TAC GCG GCA        1126
Arg Gly Ala Gln Ile Ala Ser Thr Gly Gln Leu Tyr Ala Ala
    280             285             290

TGG AAT GGC GGC TTG GAC AGA TGT AGC CCT GGC TGG CTG GCT        1168
Trp Asn Gly Gly Leu Asp Arg Cys Ser Pro Gly Trp Leu Ala
295             300             305

GAT GGC AGT GTG CGG TAC CCC ATC ATC ACG CCC AGC CAA CGC        1210
Asp Gly Ser Val Arg Tyr Pro Ile Ile Thr Pro Ser Gln Arg
        310             315             320

TGT GGG GGA GGC CTG CCA GGA GTC AAG ACC CTC TTC CTC TTT        1252
Cys Gly Gly Gly Leu Pro Gly Val Lys Thr Leu Phe Leu Phe
            325             330

CCC AAC CAG ACT GGC TTC CCC AGC AAG CAG AAC CGC TTC AAT        1294
Pro Asn Gln Thr Gly Phe Pro Ser Lys Gln Asn Arg Phe Asn
335             340             345

GTC TAC TGC TTC CGA GAC TCT GCC CAT CCC TCT GCC TTC TCT        1336
Val Tyr Cys Phe Arg Asp Ser Ala His Pro Ser Ala Phe Ser
        350             355             360

GAG CCT CCA GCC CAG CCT CTG ATG GAC TAGAGGCCAT TGTCACAGTG      1383
Glu Pro Pro Ala Gln Pro Leu Met Asp
            365             370

ACAGAGAAGC TGGAGGAACT GCAGTTGCCT CAGGAAGCTG TGGAGAGCGA         1433

GTCTCGTGGG GCGATCTACT CCATCCCCAT CACAGAAGAT GGGGGAGGAG         1483

GAAGCTCTAC CCCAGAAGAC CCAGCAGAGG CCCCCAG                       1520
```

( 2 ) INFORMATION FOR SEQ ID NO:2:

( i ) SEQUENCE CHARACTERISTICS:
        ( A ) LENGTH: 1519 bases
        ( B ) TYPE: nucleic acid
        ( C ) STRANDEDNESS: double
        ( D ) TOPOLOGY: linear ( i i ) MOLECULE TYPE:
        ( A ) DESCRIPTION: DNA encoding a protein ( v ) FRAGMENT TYPE: entire sequence ( v i ) IMMEDIATE SOURCE: cat cortex ( i x ) FEATURE:
        ( A ) NAME/KEY: cat brain BEHAB ( x i ) SEQUENCE DESCRIPTION: SEQ ID NO:2:

```
                                        CGGCACGAG CTCGTGCCGA        19

ATTCGGCACA GAGGGACCGA GCGTGGACCC GGAGGAGAGC CCGGAGGAGA             69

GCCCGGAGGA GGCGCAAACT TGGCGGTGCG CACCCTAGCC CCGGCCCTCG            119

GCCTGCCGGA AGAAAACAAA GGCCCTGAGA GCTTAAGGAA CTTGCAGCAA            169

GTTGACTAGC GCCCAGGTCT TGGTTCCGAG GAGGAATCCT GGTGGGGAGA            219

CAGGATCAGA AGCGAGGGTG TTAACAGTGA GTCCTTCCAG CAGCCTGAGC            269

ATG GCC CCA CTG TTC CTG CCC CTG CTG ATA GCC CTG GCC CTG           311
Met Ala Pro Leu Phe Leu Pro Leu Leu Ile Ala Leu Ala Leu
            5               10

GCC CCG GGC CCC ACG GCC TCA GCT GAT GTC CTG GAA GGG GAC           353
Ala Pro Gly Pro Thr Ala Ser Ala Asp Val Leu Glu Gly Asp
15              20              25
```

```
AGC  TCA  GAG  GAC  CGG  GCC  TTC  CGC  GTG  CGC  ATC  TCG  GGC  AAC        395
Ser  Ser  Glu  Asp  Arg  Ala  Phe  Arg  Val  Arg  Ile  Ser  Gly  Asn
     30                       35                      40

GCG  CCG  CTG  CAG  GGC  GTG  CTG  GGC  GGC  GCC  CTC  ACC  ATC  TCG        437
Ala  Pro  Leu  Gln  Gly  Val  Leu  Gly  Gly  Ala  Leu  Thr  Ile  Ser
          45                       50                      55

TGC  CAC  GTT  CAC  TAC  CTG  CGG  CCG  CCG  GGC  CGC  CGG  GCC             479
Cys  His  Val  His  Tyr  Leu  Arg  Pro  Pro  Pro  Gly  Arg  Arg  Ala
               60                       65                      70

GTG  CTG  GGC  TCC  CCG  CGG  GTC  AAG  TGG  ACC  TTC  CTG  TCC  GGG        521
Val  Leu  Gly  Ser  Pro  Arg  Val  Lys  Trp  Thr  Phe  Leu  Ser  Gly
                    75                       80

GGC  CGG  GAG  GCC  GAG  GTG  CTG  GTG  GCG  CGG  GGG  CTG  CGC  GTC        563
Gly  Arg  Glu  Ala  Glu  Val  Leu  Val  Ala  Arg  Gly  Leu  Arg  Val
85                        90                       95

AAG  GTG  AGC  GAG  GCC  TAC  CGG  TTC  CGC  GTG  GCG  CTG  CCC  GCC        605
Lys  Val  Ser  Glu  Ala  Tyr  Arg  Phe  Arg  Val  Ala  Leu  Pro  Ala
     100                      105                     110

TAC  CCG  GCG  TCC  CTC  ACC  GAC  GTC  TCC  CTG  GCA  CTG  AGC  GAG        647
Tyr  Pro  Ala  Ser  Leu  Thr  Asp  Val  Ser  Leu  Ala  Leu  Ser  Glu
          115                      120                     125

CTG  CGG  CCC  AAC  GAC  TCT  GGC  ATC  TAC  CGC  TGC  GAG  GTC  CAG        689
Leu  Arg  Pro  Asn  Asp  Ser  Gly  Ile  Tyr  Arg  Cys  Glu  Val  Gln
               130                      135                     140

CAC  GGC  ATA  GAC  GAC  AGC  AGC  GAC  GCC  GTG  GAG  GTC  AAG  GTC        731
His  Gly  Ile  Asp  Asp  Ser  Ser  Asp  Ala  Val  Glu  Val  Lys  Val
                    145                      150

AAA  GGG  GTC  GTC  TTT  CTC  TAC  CGG  GAG  GGC  TCT  GCC  CGC  TAC        773
Lys  Gly  Val  Val  Phe  Leu  Tyr  Arg  Glu  Gly  Ser  Ala  Arg  Tyr
155                      160                      165

GCT  TTC  TCC  TTC  GCC  CGG  GCC  CAG  GAG  GCC  TGT  GCC  CGC  ATC        815
Ala  Phe  Ser  Phe  Ala  Arg  Ala  Gln  Glu  Ala  Cys  Ala  Arg  Ile
     170                      175                     180

GGA  GCC  CGC  ATC  GCC  ACC  CCG  GAG  CAG  CTC  TAC  GCT  GCC  TAC        857
Gly  Ala  Arg  Ile  Ala  Thr  Pro  Glu  Gln  Leu  Tyr  Ala  Ala  Tyr
          185                      190                     195

CTC  GGG  GGC  TAT  GAG  CAG  TGC  GAT  GCT  GGC  TGG  CTG  TCC  GAC        899
Leu  Gly  Gly  Tyr  Glu  Gln  Cys  Asp  Ala  Gly  Trp  Leu  Ser  Asp
               200                      205                     210

CAA  ACC  GTG  AGG  TAT  CCC  ATC  CAG  ACC  CCA  CGG  GAG  GCC  TGT        941
Gln  Thr  Val  Arg  Tyr  Pro  Ile  Gln  Thr  Pro  Arg  Glu  Ala  Cys
                    215                      220

TAT  GGA  GAC  ATG  GAT  GGC  TTC  CCT  GGG  GTC  CGG  AAC  TAT  GGC        983
Tyr  Gly  Asp  Met  Asp  Gly  Phe  Pro  Gly  Val  Arg  Asn  Tyr  Gly
225                      230                      235

CTG  GTG  GAC  CCG  GAT  GAC  CTG  TAC  GAT  ATC  TAC  TGC  TAT  GCT       1025
Leu  Val  Asp  Pro  Asp  Asp  Leu  Tyr  Asp  Ile  Tyr  Cys  Tyr  Ala
     240                      245                     250

GAA  GAC  CTA  AAT  GGA  GAG  CTG  TTC  CTG  GGC  GCC  CCT  CCA  GAC       1067
Glu  Asp  Leu  Asn  Gly  Glu  Leu  Phe  Leu  Gly  Ala  Pro  Pro  Asp
          255                      260                     265

AAC  GTG  ACG  CTG  GAG  GAG  GCT  ACG  GCA  TAC  TGC  CGT  GAG  CGG       1109
Asn  Val  Thr  Leu  Glu  Glu  Ala  Thr  Ala  Tyr  Cys  Arg  Glu  Arg
               270                      275                     280

GGT  GCA  GAG  ATT  GCT  ACC  ACG  GGC  CAG  CTG  TAT  GCA  GCC  TGG       1151
Gly  Ala  Glu  Ile  Ala  Thr  Thr  Gly  Gln  Leu  Tyr  Ala  Ala  Trp
                    285                      290

GAT  GGC  GGC  CTG  GAC  CGC  TGC  AGC  CCC  GGC  TGG  CTG  GCC  GAT       1193
Asp  Gly  Gly  Leu  Asp  Arg  Cys  Ser  Pro  Gly  Trp  Leu  Ala  Asp
295                      300                      305
```

```
GGC  AGC  GTG  CGC  TAC  CCC  ATC  GTC  ACG  CCC  AGC  CAG  CGC  TGC           1235
Gly  Ser  Val  Arg  Tyr  Pro  Ile  Val  Thr  Pro  Ser  Gln  Arg  Cys
     310                     315                     320

GGT  GGG  GGC  CTG  CCT  GGC  GTC  AAG  ACT  CTC  TTC  CTC  TTC  CCC           1277
Gly  Gly  Gly  Leu  Pro  Gly  Val  Lys  Thr  Leu  Phe  Leu  Phe  Pro
          325                     330                     335

AAC  CAG  ACC  GGC  TTC  CCC  AAC  AAG  TAC  AGC  CGC  TTC  AAC  GTC           1319
Asn  Gln  Thr  Gly  Phe  Pro  Asn  Lys  Tyr  Ser  Arg  Phe  Asn  Val
               340                     345                     350

TAC  TGC  TTC  CGA  GAC  TCT  GGC  CAG  CCC  TCC  ACC  ACC  CCT  GAG           1361
Tyr  Cys  Phe  Arg  Asp  Ser  Gly  Gln  Pro  Ser  Thr  Thr  Pro  Glu
                    355                     360

GCC  TCT  GAC  CAG  CCT  CTG  ACG  GGC  TGG  AGG  CCA  TTG  TCA  CAG           1403
Ala  Ser  Asp  Gln  Pro  Leu  Thr  Gly  Trp  Arg  Pro  Leu  Ser  Gln
365                     370                     375

TGACAGAGAC  CCTAGAGGAG  CTCCACGTGC  CGCGGGAAGC  TGTGGAGAGC                     1453

GAGTCCCGGG  GAGCCATCTA  CTCCGTCCCC  ATTGTGGAGG  ATGGGGAGGT                     1503

GCAAGGTCCC  CCTCCA                                                             1519
```

( 2 ) INFORMATION FOR SEQ ID NO:3:

( i ) SEQUENCE CHARACTERISTICS:
        ( A ) LENGTH: 329 residues
        ( B ) TYPE: amino acid
        ( C ) STRANDEDNESS: single
        ( D ) TOPOLOGY: linear ( i i ) MOLECULE TYPE:
        ( A ) DESCRIPTION: polypeptide ( v ) FRAGMENT TYPE: functional domains ( i x ) FEATURE:
        ( A ) NAME/KEY: rat aggrecan ( x ) PUBLICATION INFORMATION:
        ( A ) AUTHORS: Doege, K., Sasaki, M., Horigan, E., Hassell, J.R., and Yamada, Y.
        ( B ) TITLE: Complete primary structure of the rat cartilage proteoglycan core protein deduced from cDNA clones.
        ( C ) JOURNAL: J. Biol. Chem.
        ( D ) VOLUME: 262
        ( F ) PAGES: 17757-17767
        ( G ) DATE: 1987

( x i ) SEQUENCE DESCRIPTION: SEQ ID NO:3:

```
Glu  Glu  Val  Pro  Asp  His  Asp  Asn  Ser  Leu  Ser  Val  Ser  Ile  Pro
                    5                   10                       15

Gln  Pro  Ser  Pro  Leu  Lys  Ala  Leu  Leu  Gly  Thr  Ser  Leu  Thr  Ile
                    20                  25                       30

Pro  Cys  Tyr  Phe  Ile  Asp  Pro  Met  His  Pro  Val  Thr  Thr  Ala  Pro
                    35                  40                       45

Ser  Thr  Ala  Pro  Leu  Thr  Arg  Ile  Lys  Trp  Ser  Arg  Val  Ser  Lys
                    50                  55                       60

Glu  Lys  Glu  Val  Val  Leu  Leu  Val  Ala  Thr  Glu  Gly  Gln  Val  Arg
                    65                  70                       75

Val  Asn  Ser  Ile  Tyr  Gln  Asp  Lys  Val  Ser  Leu  Pro  Asn  Tyr  Pro
                    80                  85                       90

Ala  Ile  Pro  Ser  Asp  Ala  Thr  Leu  Glu  Ile  Gln  Asn  Leu  Arg  Ser
                    95                  100                      105

Asn  Asp  Ser  Gly  Ile  Tyr  Arg  Cys  Glu  Val  Met  His  Gly  Ile  Glu
                    110                 115                      120
```

| | | | | | | | | | | | | | | | |
|---|---|---|---|---|---|---|---|---|---|---|---|---|---|---|---|
| Asp | Ser | Glu | Ala | Thr<br>125 | Leu | Glu | Val | Ile | Val<br>130 | Lys | Gly | Ile | Val | Phe<br>135 |
| His | Tyr | Arg | Ala | Ile<br>140 | Ser | Thr | Arg | Tyr | Thr<br>145 | Leu | Asp | Phe | Asp | Arg<br>150 |
| Ala | Gln | Arg | Ala | Cys<br>155 | Leu | Gln | Asn | Ser | Ala<br>160 | Ile | Ile | Ala | Thr | Pro<br>165 |
| Glu | Gln | Leu | Gln | Ala<br>170 | Ala | Tyr | Glu | Asp | Gly<br>175 | Phe | His | Gln | Cys | Asp<br>180 |
| Ala | Gly | Trp | Leu | Ala<br>185 | Asp | Gln | Thr | Val | Arg<br>190 | Tyr | Pro | Ile | His | Thr<br>195 |
| Pro | Arg | Glu | Gly | Cys<br>200 | Tyr | Gly | Asp | Lys | Asp<br>205 | Glu | Phe | Pro | Gly | Val<br>210 |
| Arg | Thr | Tyr | Gly | Ile<br>215 | Arg | Asp | Thr | Asn | Glu<br>220 | Thr | Tyr | Asp | Val | Tyr<br>225 |
| Cys | Phe | Ala | Glu | Glu<br>230 | Met | Glu | Gly | Glu | Phe<br>235 | Tyr | Ala | Thr | Ser | Pro<br>240 |
| Glu | Lys | Phe | Thr | Phe<br>245 | Gln | Glu | Ala | Ala | Asn<br>250 | Glu | Cys | Arg | Thr | Val<br>255 |
| Gly | Ala | Arg | Leu | Ala<br>260 | Thr | Thr | Gly | Gln | Leu<br>265 | Tyr | Leu | Ala | Trp | Gln<br>270 |
| Gly | Gly | Met | Asp | Met<br>275 | Cys | Ser | Ala | Gly | Trp<br>280 | Leu | Ala | Asp | Arg | Ser<br>285 |
| Val | Arg | Tyr | Pro | Ile<br>290 | Ser | Lys | Ala | Arg | Pro<br>295 | Asn | Cys | Gly | Gly | Asn<br>300 |
| Leu | Leu | Gly | Val | Arg<br>305 | Thr | Val | Tyr | Leu | His<br>310 | Ala | Asn | Gln | Thr | Gly<br>315 |
| Tyr | Pro | Asp | Pro | Ser<br>320 | Ser | Arg | Tyr | Asp | Ala<br>325 | Ile | Cys | Tyr | Thr | |

(2) INFORMATION FOR SEQ ID NO:4:

(i) SEQUENCE CHARACTERISTICS:
        (A) LENGTH: 333 residues
        (B) TYPE: amino acid
        (C) STRANDEDNESS: single
        (D) TOPOLOGY: linear (ii) MOLECULE TYPE:
        (A) DESCRIPTION: polypeptide (v) FRAGMENT TYPE: functional domains (ix) FEATURE:
        (A) NAME/KEY: rat neurocan (x) PUBLICATION INFORMATION:
        (A) AUTHORS: Rauch, U., Karthikeyan, L.,
            Maurel, P., Margolis, R.U., and Margolis,
            R.K.
        (B) TITLE: Cloning and primary structure of neurocan, a developmentally regulated, aggregating chondroitin sulfate proteoglycan of brain.
        (C) JOURNAL: J. Biol. Chem.
        (D) VOLUME: 267
        (F) PAGES: 19536-19547
        (G) DATE: 1992

(xi) SEQUENCE DESCRIPTION: SEQ ID NO:4:

| | | | | | | | | | | | | | | | |
|---|---|---|---|---|---|---|---|---|---|---|---|---|---|---|---|
| Asp | Thr | Gln | Asp | Thr<br>5 | Thr | Thr | Thr | Glu | Lys<br>10 | Gly | Leu | His | Met | Leu<br>15 |
| Lys | Ser | Gly | Ser | Gly<br>20 | Pro | Ile | Gln | Ala | Ala<br>25 | Leu | Ala | Glu | Leu | Val<br>30 |

| | | | | | | | | | | | | | | |
|---|---|---|---|---|---|---|---|---|---|---|---|---|---|---|
|Ala|Leu|Pro|Cys|Phe 35|Phe|Thr|Leu|Gln|Pro 40|Arg|Gln|Ser|Pro|Leu 45|
|Gly|Asp|Ile|Pro|Arg 50|Ile|Lys|Trp|Thr|Lys 55|Val|Gln|Thr|Ala|Ser 60|
|Gly|Gln|Arg|Gln|Asp 65|Leu|Pro|Ile|Leu|Val 70|Ala|Lys|Asp|Asn|Val 75|
|Val|Arg|Val|Ala|Lys 80|Gly|Trp|Gln|Gly|Arg 85|Val|Ser|Leu|Pro|Ala 90|
|Tyr|Pro|Arg|His|Arg 95|Ala|Asn|Ala|Thr|Leu 100|Leu|Leu|Gly|Pro|Leu 105|
|Arg|Ala|Ser|Asp|Ser 110|Gly|Leu|Tyr|Arg|Cys 115|Gln|Val|Val|Lys|Gly 120|
|Ile|Glu|Asp|Glu|Gln 125|Asp|Leu|Val|Thr|Leu 130|Glu|Val|Thr|Gly|Val 135|
|Val|Phe|His|Tyr|Arg 140|Ala|Ala|Arg|Asp|Arg 145|Tyr|Ala|Leu|Thr|Phe 150|
|Ala|Glu|Ala|Gln|Glu 155|Ala|Cys|His|Leu|Ser 160|Ser|Ala|Thr|Ile|Ala 165|
|Ala|Pro|Arg|His|Leu 170|Asn|Ala|Ala|Phe|Glu 175|Asp|Gly|Phe|Asp|Asn 180|
|Cys|Asp|Ala|Gly|Trp 185|Leu|Ser|Asp|Arg|Thr 190|Val|Arg|Tyr|Pro|Ile 195|
|Thr|Gln|Ser|Arg|Pro 200|Gly|Cys|Tyr|Gly|Asp 205|Arg|Ser|Ser|Leu|Pro 210|
|Gly|Val|Arg|Ser|Tyr 215|Gly|Arg|Arg|Asp|Pro 220|Gln|Glu|Leu|Tyr|Asp 225|
|Val|Tyr|Cys|Phe|Ala 230|Arg|Glu|Leu|Gly|Gly 235|Glu|Phe|Tyr|Val|Gly 240|
|Pro|Ala|Arg|Arg|Leu 245|Thr|Leu|Ala|Gly|Ala 250|Arg|Ala|Leu|Cys|Gln 255|
|Arg|Gln|Gly|Ala|Ala 260|Leu|Ala|Ser|Val|Gly 265|Gln|Leu|His|Leu|Ala 270|
|Trp|His|Glu|Gly|Leu 275|Asp|Gln|Cys|Asp|Pro 280|Gly|Trp|Leu|Ala|Asp 285|
|Gly|Ser|Val|Arg|Tyr 290|Pro|Ile|Gln|Thr|Pro 295|Arg|Arg|Arg|Cys|Gly 300|
|Gly|Ser|Ala|Pro|Gly 305|Val|Arg|Thr|Val|Tyr 310|Arg|Phe|Ala|Asn|Arg 315|
|Thr|Gly|Phe|Pro|Ala 320|Pro|Gly|Ala|Arg|Phe 325|Asp|Ala|Tyr|Cys|Phe 330|
|Arg|Ala|His| | | | | | | | | | | | |

( 2 ) INFORMATION FOR SEQ ID NO:5:

( i ) SEQUENCE CHARACTERISTICS:
        ( A ) LENGTH: 328 residues
        ( B ) TYPE: amino acid
        ( C ) STRANDEDNESS: single
        ( D ) TOPOLOGY: linear ( i i ) MOLECULE TYPE:
        ( A ) DESCRIPTION: polypeptide ( v ) FRAGMENT TYPE: functional domains ( i x ) FEATURE:
        ( A ) NAME/KEY: human versican ( x ) PUBLICATION INFORMATION:

(A) AUTHORS: Zimmermann, D.R., and Ruoslahti, E.
(B) TITLE: Multiple domains of the large fibro-
        blast proteoglycan, versican.
(C) JOURNAL: EMBO (Eur. Mol. Biol. Organ.) J.
(D) VOLUME: 8
(F) PAGES: 2975-2981
(G) DATE: 1989

(xi) SEQUENCE DESCRIPTION: SEQ ID NO:5:

| | | | | | | | | | | | | | | |
|---|---|---|---|---|---|---|---|---|---|---|---|---|---|---|
| Leu | His | Lys | Val | Lys<br>5 | Val | Gly | Lys | Ser | Pro<br>10 | Pro | Val | Arg | Gly | Ser<br>15 |
| Leu | Ser | Gly | Lys | Val<br>20 | Ser | Leu | Pro | Cys | His<br>25 | Phe | Ser | Thr | Met | Pro<br>30 |
| Thr | Leu | Pro | Pro | Ser<br>35 | Tyr | Asn | Thr | Ser | Glu<br>40 | Phe | Leu | Arg | Ile | Lys<br>45 |
| Trp | Ser | Lys | Ile | Glu<br>50 | Val | Asp | Lys | Asn | Gly<br>55 | Lys | Asp | Leu | Lys | Glu<br>60 |
| Thr | Thr | Val | Leu | Val<br>65 | Ala | Gln | Asn | Gly | Asn<br>70 | Ile | Lys | Ile | Gly | Gln<br>75 |
| Asp | Tyr | Lys | Gly | Arg<br>80 | Val | Ser | Val | Pro | Thr<br>85 | His | Pro | Glu | Ala | Val<br>90 |
| Gly | Asp | Ala | Ser | Leu<br>95 | Thr | Val | Val | Lys | Leu<br>100 | Leu | Ala | Ser | Asp | Ala<br>105 |
| Gly | Leu | Tyr | Arg | Cys<br>110 | Asp | Val | Met | Tyr | Gly<br>115 | Ile | Glu | Asp | Thr | Gln<br>120 |
| Asp | Thr | Val | Ser | Leu<br>125 | Thr | Val | Asp | Gly | Val<br>130 | Val | Phe | His | Tyr | Arg<br>135 |
| Ala | Ala | Thr | Ser | Arg<br>140 | Tyr | Thr | Leu | Asn | Phe<br>145 | Glu | Ala | Ala | Gln | Lys<br>150 |
| Ala | Cys | Leu | Asp | Val<br>155 | Gly | Ala | Val | Ile | Ala<br>160 | Thr | Pro | Glu | Gln | Leu<br>165 |
| Phe | Ala | Ala | Tyr | Glu<br>170 | Asp | Gly | Phe | Glu | Gln<br>175 | Cys | Asp | Ala | Gly | Trp<br>180 |
| Leu | Ala | Asp | Gln | Thr<br>185 | Val | Arg | Tyr | Pro | Ile<br>190 | Arg | Ala | Pro | Arg | Val<br>195 |
| Gly | Cys | Tyr | Gly | Asp<br>200 | Lys | Met | Gly | Lys | Ala<br>205 | Gly | Val | Arg | Thr | Tyr<br>210 |
| Gly | Phe | Arg | Ser | Pro<br>215 | Gln | Glu | Thr | Tyr | Asp<br>220 | Val | Tyr | Cys | Tyr | Val<br>225 |
| Asp | His | Leu | Asp | Gly<br>230 | Asp | Phe | His | Leu | Thr<br>235 | Val | Pro | Ser | Lys | Phe<br>240 |
| Thr | Phe | Glu | Glu | Ala<br>245 | Ala | Lys | Glu | Cys | Glu<br>250 | Asn | Gln | Asp | Ala | Arg<br>255 |
| Leu | Ala | Thr | Val | Gly<br>260 | Glu | Leu | Gln | Ala | Ala<br>265 | Trp | Arg | Asn | Gly | Phe<br>270 |
| Asp | Gln | Cys | Asp | Tyr<br>275 | Gly | Trp | Leu | Ser | Asp<br>280 | Ala | Ser | Val | Arg | His<br>285 |
| Pro | Val | Thr | Val | Ala<br>290 | Arg | Ala | Gln | Cys | Gly<br>295 | Gly | Gly | Leu | Leu | Gly<br>300 |
| Val | Arg | Thr | Leu | Tyr<br>305 | Arg | Phe | Glu | Asn | Gln<br>310 | Thr | Gly | Phe | Pro | Pro<br>315 |
| Pro | Asp | Ser | Arg | Phe<br>320 | Asp | Ala | Tyr | Cys | Phe<br>325 | Lys | Arg | Arg | | |

(2) INFORMATION FOR SEQ ID NO:6:

(i) SEQUENCE CHARACTERISTICS:

(A) LENGTH: 326 residues
(B) TYPE: amino acid
(C) STRANDEDNESS: single
(D) TOPOLOGY: linear (ii) MOLECULE TYPE:
(A) DESCRIPTION: polypeptide (v) FRAGMENT TYPE: functional domains (ix) FEATURE:
(A) NAME/KEY: rat link protein (x) PUBLICATION INFORMATION:
(A) AUTHORS: Doege, K., Hassell, J.R., Caterson, B., and Yamada, Y.
(B) TITLE: Link protein cDNA sequence reveals a tandemly repeated protein sequence.
(C) JOURNAL: Proc. Natl. Acad. Sci. USA
(D) VOLUME: 83
(F) PAGES: 3761-3765
(G) DATE: 1986

(xi) SEQUENCE DESCRIPTION: SEQ ID NO:6:

```
Asp Arg Val Ile His Ile Gln Ala Glu Asn Gly Pro Arg Leu Leu
              5                  10                  15
Val Glu Ala Glu Gln Ala Lys Val Phe Ser His Arg Gly Gly Asn
             20                  25                  30
Val Thr Leu Pro Cys Lys Phe Tyr Arg Asp Pro Thr Ala Phe Gly
             35                  40                  45
Ser Gly Ile His Lys Ile Arg Ile Lys Trp Thr Lys Leu Thr Ser
             50                  55                  60
Asp Tyr Leu Arg Glu Val Asp Val Phe Val Ser Met Gly Tyr His
             65                  70                  75
Lys Lys Thr Tyr Gly Gly Tyr Gln Gly Arg Val Phe Leu Lys Gly
             80                  85                  90
Gly Ser Asp Asn Asp Ala Ser Leu Ile Ile Thr Asp Leu Thr Leu
             95                 100                 105
Glu Asp Tyr Gly Arg Tyr Lys Cys Glu Val Ile Glu Gly Leu Glu
            110                 115                 120
Asp Asp Thr Ala Val Val Ala Leu Glu Leu Gln Gly Val Val Phe
            125                 130                 135
Pro Tyr Phe Pro Arg Leu Gly Arg Tyr Asn Leu Asn Phe His Glu
            140                 145                 150
Ala Arg Gln Ala Cys Leu Asp Gln Asp Ala Val Ile Ala Ser Phe
            155                 160                 165
Asp Gln Leu Tyr Asp Ala Trp Arg Gly Gly Leu Asp Trp Cys Asn
            170                 175                 180
Ala Gly Trp Leu Ser Asp Gly Ser Val Gln Tyr Pro Ile Thr Lys
            185                 190                 195
Pro Arg Glu Pro Cys Gly Gly Gln Asn Thr Val Pro Gly Val Arg
            200                 205                 210
Asn Tyr Gly Phe Trp Asp Lys Asp Ser Arg Tyr Asp Val Phe Cys
            215                 220                 225
Phe Thr Ser Asn Phe Asn Gly Arg Phe Tyr Tyr Leu Ile His Pro
            230                 235                 240
Thr Lys Leu Thr Tyr Asp Glu Ala Val Gln Ala Cys Leu Asn Asp
            245                 250                 255
Gly Ala Gln Ile Ala Lys Val Gly Gln Ile Phe Ala Ala Trp Lys
            260                 265                 270
```

```
Leu Leu Gly Tyr Asp Arg Cys Asp Ala Gly Trp Leu Ala Asp Gly
            275                 280                 285

Ser Val Arg Tyr Pro Ile Ser Arg Pro Trp Arg Arg Cys Ser Pro
            290                 295                 300

Thr Glu Ala Ala Val Arg Phe Val Gly Phe Pro Asp Lys Lys His
            305                 310                 315

Lys Leu Tyr Gly Val Tyr Cys Phe Arg Ala Tyr
            320                 325
```

( 2 ) INFORMATION FOR SEQ ID NO:7:

( i ) SEQUENCE CHARACTERISTICS:
    ( A ) LENGTH: 156 bases
    ( B ) TYPE: nucleic acid
    ( C ) STRANDEDNESS: double
    ( D ) TOPOLOGY: linear ( i i ) MOLECULE TYPE:
    ( A ) DESCRIPTION: DNA encoding a polypeptide ( v ) FRAGMENT TYPE: partial sequence, PTR1 domain ( v i ) IMMEDIATE SOURCE: human brain ( i x ) FEATURE:
    ( A ) NAME/KEY: human BEHAB ( x i ) SEQUENCE DESCRIPTION: SEQ ID NO:7:

```
GAG AGG GCT CTG CGC TAT GCT TTC TCC TTT TCT GGG GCC CAG        42
Glu Arg Ala Leu Arg Tyr Ala Phe Ser Phe Ser Gly Ala Gln
            5                   10

GAG GCT TGT GCC CGC ATT GGA GCC CAC ATC GCC ACC CCG GAG        84
Glu Ala Cys Ala Arg Ile Gly Ala His Ile Ala Thr Pro Glu
 15                 20                  25

CAG CTC TAT GCC GCC TAC CTT GGG GGC TAT GAG CAA TGT GAT       126
Gln Leu Tyr Ala Ala Tyr Leu Gly Gly Tyr Glu Gln Cys Asp
    30                  35                  40

GCT GGC TGG CTG TCG GAT CAG ACC GTG AGA                       156
Ala Gly Trp Leu Ser Asp Gln Thr Val Arg
        45                  50
```

( 2 ) INFORMATION FOR SEQ ID NO:8:

( i ) SEQUENCE CHARACTERISTICS:
    ( A ) LENGTH: 371 amino acids
    ( B ) TYPE: amino acid
    ( C ) STRANDEDNESS: single
    ( D ) TOPOLOGY: linear ( i i ) MOLECULE TYPE:
    ( A ) DESCRIPTION: polypeptide ( v ) FRAGMENT TYPE: entire sequence ( v i ) IMMEDIATE SOURCE: rat brain ( i x ) FEATURE:
    ( A ) NAME/KEY: rat BEHAB
    ( D ) OTHER INFORMATION: polypeptide encoded by (and set out under) SEQ ID NO 1

( x i ) SEQUENCE DESCRIPTION: SEQ ID NO:8:

```
        Met Ile Pro Leu Leu Ser Leu Leu Ala Ala Leu
                        5                   10

Val Leu Thr Gln Ala Pro Ala Ala Leu Ala Asp Asp Leu Lys
                15                  20                  25

Glu Asp Ser Ser Glu Asp Arg Ala Phe Arg Val Arg Ile Gly
                    30                  35                  40
```

```
Ala Ala Gln Leu Arg Gly Val Leu Gly Gly Trp Val Ala Ile
             45                      50

Pro Cys His Val His Leu Arg Pro Pro Pro Ser Arg Arg
 55              60                  65

Ala Ala Pro Gly Phe Pro Arg Val Lys Trp Thr Phe Leu Ser
     70              75              80

Gly Asp Arg Glu Val Glu Val Leu Val Ala Arg Gly Leu Arg
         85              90              95

Val Lys Val Asn Glu Ala Tyr Arg Phe Arg Val Ala Leu Pro
            100             105             110

Ala Tyr Pro Ala Ser Leu Thr Asp Val Ser Leu Val Leu Ser
                115             120

Glu Leu Arg Pro Asn Asp Ser Gly Val Tyr Arg Cys Glu Val
125             130             135

Gln His Gly Ile Asp Asp Ser Ser Asp Ala Val Glu Val Lys
        140             145             150

Val Lys Gly Val Val Phe Leu Tyr Arg Glu Gly Ser Ala Arg
            155             160             165

Tyr Ala Phe Ser Phe Ala Gly Ala Gln Glu Ala Cys Ala Arg
            170             175             180

Ile Gly Ala Arg Ile Ala Thr Pro Glu Gln Leu Tyr Ala Ala
            185             190

Tyr Leu Gly Gly Tyr Glu Gln Cys Asp Ala Gly Trp Leu Ser
195             200             205

Asp Gln Thr Val Arg Tyr Pro Ile Gln Asn Pro Arg Glu Ala
    210             215             220

Cys Tyr Gly Asp Met Asp Gly Tyr Pro Gly Val Arg Asn Tyr
        225             230             235

Gly Val Val Gly Pro Asp Asp Leu Tyr Asp Val Tyr Cys Tyr
            240             245             250

Ala Glu Asp Leu Asn Gly Glu Leu Phe Leu Gly Ala Pro Pro
                255             260

Gly Lys Leu Thr Trp Glu Glu Ala Arg Asp Tyr Cys Leu Glu
265             270             275

Arg Gly Ala Gln Ile Ala Ser Thr Gly Gln Leu Tyr Ala Ala
    280             285             290

Trp Asn Gly Gly Leu Asp Arg Cys Ser Pro Gly Trp Leu Ala
    295             300             305

Asp Gly Ser Val Arg Tyr Pro Ile Ile Thr Pro Ser Gln Arg
            310             315             320

Cys Gly Gly Gly Leu Pro Gly Val Lys Thr Leu Phe Leu Phe
            325             330

Pro Asn Gln Thr Gly Phe Pro Ser Lys Gln Asn Arg Phe Asn
335             340             345

Val Tyr Cys Phe Arg Asp Ser Ala His Pro Ser Ala Phe Ser
    350             355             360

Glu Pro Pro Ala Gln Pro Leu Met Asp
        365             370
```

( 2 ) INFORMATION FOR SEQ ID NO:9:

( i ) SEQUENCE CHARACTERISTICS:
        ( A ) LENGTH: 378 amino acids
        ( B ) TYPE: amino acid
        ( C ) STRANDEDNESS: single ( D ) TOPOLOGY: linear ( i i ) MOLECULE TYPE:
  ( A ) DESCRIPTION: polypeptide ( v ) FRAGMENT TYPE: entire sequence ( v i ) IMMEDIATE SOURCE: cat cortex ( i x ) FEATURE:
  ( A ) NAME/KEY: cat brain BEHAB
  ( B ) OTHER INFORMATION: polypeptide encoded by (and set out under) SEQ ID NO 2

( x i ) SEQUENCE DESCRIPTION: SEQ ID NO:9:

```
Met Ala Pro Leu Phe Leu Pro Leu Leu Ile Ala Leu Ala Leu
                  5                   10

Ala Pro Gly Pro Thr Ala Ser Ala Asp Val Leu Glu Gly Asp
 15                  20                  25

Ser Ser Glu Asp Arg Ala Phe Arg Val Arg Ile Ser Gly Asn
     30                  35                  40

Ala Pro Leu Gln Gly Val Leu Gly Gly Ala Leu Thr Ile Ser
         45                  50                  55

Cys His Val His Tyr Leu Arg Pro Pro Pro Gly Arg Arg Ala
             60                  65                  70

Val Leu Gly Ser Pro Arg Val Lys Trp Thr Phe Leu Ser Gly
                 75                  80

Gly Arg Glu Ala Glu Val Leu Val Ala Arg Gly Leu Arg Val
 85                  90                  95

Lys Val Ser Glu Ala Tyr Arg Phe Arg Val Ala Leu Pro Ala
100                 105                 110

Tyr Pro Ala Ser Leu Thr Asp Val Ser Leu Ala Leu Ser Glu
        115                 120                 125

Leu Arg Pro Asn Asp Ser Gly Ile Tyr Arg Cys Glu Val Gln
            130                 135                 140

His Gly Ile Asp Asp Ser Ser Asp Ala Val Glu Val Lys Val
                145                 150

Lys Gly Val Val Phe Leu Tyr Arg Glu Gly Ser Ala Arg Tyr
155                 160                 165

Ala Phe Ser Phe Ala Arg Ala Gln Glu Ala Cys Ala Arg Ile
    170                 175                 180

Gly Ala Arg Ile Ala Thr Pro Glu Gln Leu Tyr Ala Ala Tyr
        185                 190                 195

Leu Gly Gly Tyr Glu Gln Cys Asp Ala Gly Trp Leu Ser Asp
            200                 205                 210

Gln Thr Val Arg Tyr Pro Ile Gln Thr Pro Arg Glu Ala Cys
                215                 220

Tyr Gly Asp Met Asp Gly Phe Pro Gly Val Arg Asn Tyr Gly
225                 230                 235

Leu Val Asp Pro Asp Asp Leu Tyr Asp Ile Tyr Cys Tyr Ala
    240                 245                 250

Glu Asp Leu Asn Gly Glu Leu Phe Leu Gly Ala Pro Pro Asp
        255                 260                 265

Asn Val Thr Leu Glu Glu Ala Thr Ala Tyr Cys Arg Glu Arg
            270                 275                 280

Gly Ala Glu Ile Ala Thr Thr Gly Gln Leu Tyr Ala Ala Trp
                285                 290
```

| Asp 295 | Gly | Gly | Leu | Asp | Arg 300 | Cys | Ser | Pro | Gly | Trp 305 | Leu | Ala | Asp |
| Gly | Ser 310 | Val | Arg | Tyr | Pro | Ile 315 | Val | Thr | Pro | Ser | Gln 320 | Arg | Cys |
| Gly | Gly | Gly 325 | Leu | Pro | Gly | Val | Lys 330 | Thr | Leu | Phe | Leu | Phe 335 | Pro |
| Asn | Gln | Thr | Gly 340 | Phe | Pro | Asn | Lys | Tyr 345 | Ser | Arg | Phe | Asn | Val 350 |
| Tyr | Cys | Phe | Arg | Asp 355 | Ser | Gly | Gln | Pro | Ser 360 | Thr | Thr | Pro | Glu |
| Ala 365 | Ser | Asp | Gln | Pro | Leu 370 | Thr | Gly | Trp | Arg | Pro 375 | Leu | Ser | Gln |

( 2 ) INFORMATION FOR SEQ ID NO:10:

( i ) SEQUENCE CHARACTERISTICS:
        ( A ) LENGTH: 52 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: polypeptide ( v ) FRAGMENT TYPE: partial sequence, PTR1 domain ( v i ) IMMEDIATE SOURCE: human brain ( i x ) FEATURE:
        ( A ) NAME/KEY: human BEHAB
        ( D ) OTHER INFORMATION: polypeptide encoded by (and set out under) SEQ ID NO 7

( x i ) SEQUENCE DESCRIPTION: SEQ ID NO:10:

| Glu | Arg | Ala | Leu | Arg 5 | Tyr | Ala | Phe | Ser | Phe 10 | Ser | Gly | Ala | Gln |
| Glu 15 | Ala | Cys | Ala | Arg | Ile 20 | Gly | Ala | His | Ile | Ala 25 | Thr | Pro | Glu |
| Gln | Leu 30 | Tyr | Ala | Ala | Tyr | Leu 35 | Gly | Gly | Tyr | Glu | Gln 40 | Cys | Asp |
| Ala | Gly | Trp 45 | Leu | Ser | Asp | Gln | Thr 50 | Val | Arg |

( 2 ) INFORMATION FOR SEQ ID NO:11:

( i ) SEQUENCE CHARACTERISTICS:
        ( A ) LENGTH: 15 residues
        ( B ) TYPE: amino acid
        ( C ) STRANDEDNESS: single
        ( D ) TOPOLOGY: linear ( i i ) MOLECULE TYPE:
        ( A ) DESCRIPTION: peptide ( v ) FRAGMENT TYPE: internal ( i x ) FEATURE:
        ( A ) NAME/KEY: conserved PTR1 and PTR 2 region
        ( D ) OTHER INFORMATION: found in PTR family's HA-binding protein domain; two copies found in BEHAB; residue 7 is Ala or Ser; residue 9 is Gln or Gly; residue 10 is Thr or Ser ( x i ) SEQUENCE DESCRIPTION: SEQ ID NO:11:

| Cys | Asp | Ala | Gly | Trp 5 | Leu | Xaa | Asp | Xaa | Xaa 10 | Val | Arg | Tyr | Pro | Ile 15 |

DNA ENCODING BEHAB, A BRAIN HYALURONAN-BINDING PROTEIN, AND RECOMBINANT EXPRESSION SYSTEMS FOR PRODUCTION OF BEHAB POLYPEPTIDES

DESCRIPTION

1. Technical Field of the Invention

This invention relates to a gene encoding a hyaluronan-binding protein that is restricted to the central nervous system, the polypeptide encoded by the gene, and methods for using the polypeptide.

2. Background of the Invention

The central nervous system extracellular matrix consists of a heterogenous mixture of glycoconjugates, many of which are proteoglycans (Jaworski, D. M., et al., *J. Cell Biol.* 125:495-509 (1994), the full text of which is hereby incorporated herein in its entirety by reference). Proteoglycans are complex macromolecules that consist of a core protein modified with one or more types of glycosaminoglycan chains.

Many functional properties of proteoglycans have been ascribed to glycosaminoglycans (ibid.). Glycosaminoglycans have been reported to exhibit both adhesive and repulsive properties and, as such, have been suggested to mediate neuronal migration and axon guidance. Glycosaminoglycans are believed to regulate the local cellular environment primarily by serving as selective filters, facilitating permeability and retention of low molecular weight solutes, including growth factors, while excluding other macromolecules.

Hyaluronan (also called hyaluronic acid or hyaluronate, and herein abbreviated HA) is particularly suited to this function because of its charge density and hydroscopic nature. HA is a negatively charged high-molecular-weight linear polysaccharide built from repeating disaccharide units (Laurent, T. C., and Fraser, J. R. E., *FASEB (Fed. Am. Soc. Expo Biol.)* 6:2397-2404 (1992)). Hyaluronan is ubiquitously distributed in the extracellular matrices of all tissues, including brain, and is believed to have several functions, including the organization of water and extracellular proteins (ibid.). During development, HA plays a role in the regulation of morphogenesis and differentiation of neural tissues.

Because HA is ubiquitously present in extracellular space, cell type specific functions attributed to HA may be mediated through its interaction with HA-binding proteins, which not only bind HA but can also contain potential binding sites for other molecules. Several HA-binding proteins in the brain have been reported, a subset of which have a high degree of sequence similarity to one another, including versican (Zimmermann, D. R., and Ruoslahti, E., *EMBO (Eur. Mol. Biol. Organ.) J.* 8: 2975-2981 (1989)), link protein (Doege, K., et al., *Proc. Natl. Acad. Sci. USA* 83:3761-3765 (1986)), neurocan (Rauch, U., et al., *J. Biol. Chem.* 267: 19536-19547 (1992)), glial hyaluronate binding protein (GHAP, Perides, G., et al., *J. Biol. Chem.* 264:5981-5987 (1989)), and CD44 (Culty, M., et al., *J. Cell Biol.* 111: 2765-2774 (1990)). These have been called the proteoglycan tandem repeat (PTR) family of HA-binding protein.

The spatial distribution and temporal expression of neural extracellular matrix proteoglycans and HA-binding proteins indicate that they may be involved in many events in the development and function of the mammalian central nervous system (Jaworski, et al., cited above) and in the modulation of cell-cell and cell-matrix interactions. While some HA-binding proteins represent general components of the extracellular matrix, others have a restricted pattern of expression on subsets of neurons. In addition, while some extracellular matrix molecules are transiently expressed during embryogenesis, others are first expressed late in the postnatal period, coincident with the decline in developmental synaptic plasticity.

It would be desirable to isolate an HA-binding protein specific to a particular tissue or organ, especially where expression of the protein varied with pathological states so that it could be used as a marker for diagnostic purposes.

SUMMARY OF THE INVENTION

It is an object of the invention to provide a gene encoding a mammalian hyaluronan-binding protein and to elucidate the relationship of the structure of the protein encoded by the gene to other polypeptides, especially other hyaluronan-binding proteins.

It is another and more specific object of the invention to provide a gene encoding a mammalian hyaluronan-binding protein that is restricted to central nervous system tissue and the polypeptide encoded by the gene.

These and other objects are accomplished by the present invention which provides purified and isolated DNA fragments comprising DNA sequences encoding mammalian brain enriched hyaluronan binding protein (herein denoted BEHAB), the polypeptide structures they encode, and the relationship of the structures to other polypeptides. Also provided are RNA sequences corresponding to the DNA sequences of the genes, biologically functional plasmids or vectors comprising the DNA or RNA sequences, and procaryotic or eucaryotic host cells transformed or transfected with the plasmids or vectors in a manner allowing the host cell to express the polypeptides.

DNA sequences encoding rat and cat BEHAB are cloned, characterized, and sequenced, and the putative amino acid sequences of the polypeptides encoded by the open reading frame are determined (SEQ ID NOs 1 and 2) and human BEHAB partially sequenced (SEQ ID NO 7). The sequence exhibits long stretches of identity between species, suggesting that the encoded protein is functionally important. Unlike other hyaluronan-binding proteins, the expression of BEHAB DNA is restricted to the central nervous system, and markedly increases in glioma. Thus, the protein can be employed as a diagnostic marker for the detection of brain tumors and other neuropathological states, and the invention encompasses methods of detection of BEHAB in biological samples.

BRIEF DESCRIPTION OF THE FIGURES

FIGS. 1A to 1B sets out sequence alignments of portions of rat BEHAB (SEQ ID NO 8), portions of cat BEHAB (SEQ ID NO 9), rat aggrecan (SEQ ID NO 3), rat neurocan (SEQ ID NO 4), human versican (SEQ ID NO 5), and rat link protein (SEQ ID NO 6). To illustrate homologous sequences, the figure employs standard one-letter nomenclature for the amino acids: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr. Identical amino acids are shown in black, and amino acid similarity is shown using stippling. The PTR proteins contain three functional domains: an inununoglobulin fold (1A), and two domains thought to be involved in hyaluronan binding, PTR1 (1B) and PTR2 (1C).

DETAILED DESCRIPTION OF THE INVENTION

This invention is based upon the identification of a new hyaluronan-binding protein, denoted BEHAB for Brain Enriched Hyaluronan Binding protein, that is restricted to the brain.

By "hyaluronan-binding" protein is meant a protein that binds hyaluronan, a viscous mucopolysaccharide having the structure [D-glucuronic acid (1-β-3)N-acetyl-D-glucosamine(1-β-4)]$_n$ (Laurent and Fraser, cited above). As described in the Examples that follow, the hyaluronan-binding proteins of this invention are restricted to central nervous system tissues, found in both white and gray matter, and are not detected in liver, kidney, spleen, lung, muscle or other tissues. Expression is elevated in human brain glioma, but is not detected in non-brain tumors, including breast, lung, and colon. The BEHAB gene encodes a neural specific protein that binds hyaluronan but lacks a transmembrane domain.

The expression of BEHAB mRNA is developmentally regulated; expression is first detected in the late embryonic period and peaks during the first two postnatal weeks. In the embryo, BEHAB is expressed at highest levels in mitotically active cells. The size and sequence of BEHAB are consistent with the possibility that it could serve a function like link protein, stabilizing interactions between hyaluronan and brain proteoglycans.

Figure 1A:
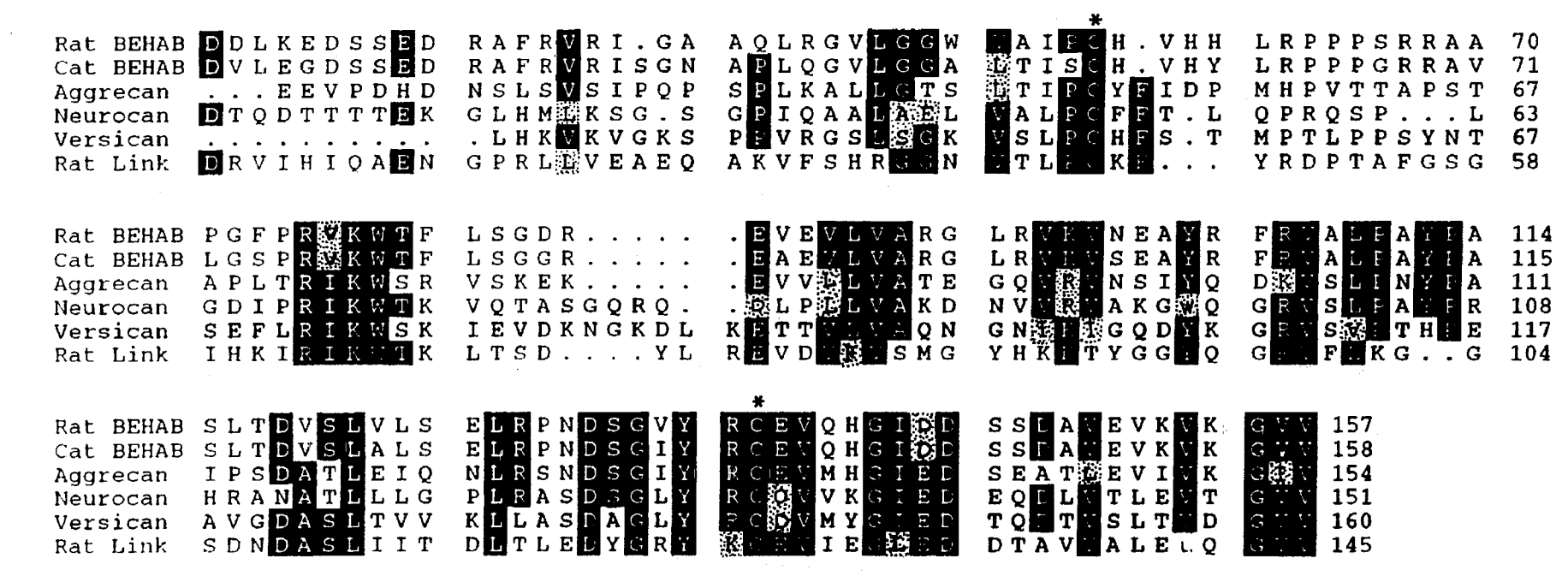
Figures 1B, 1C:
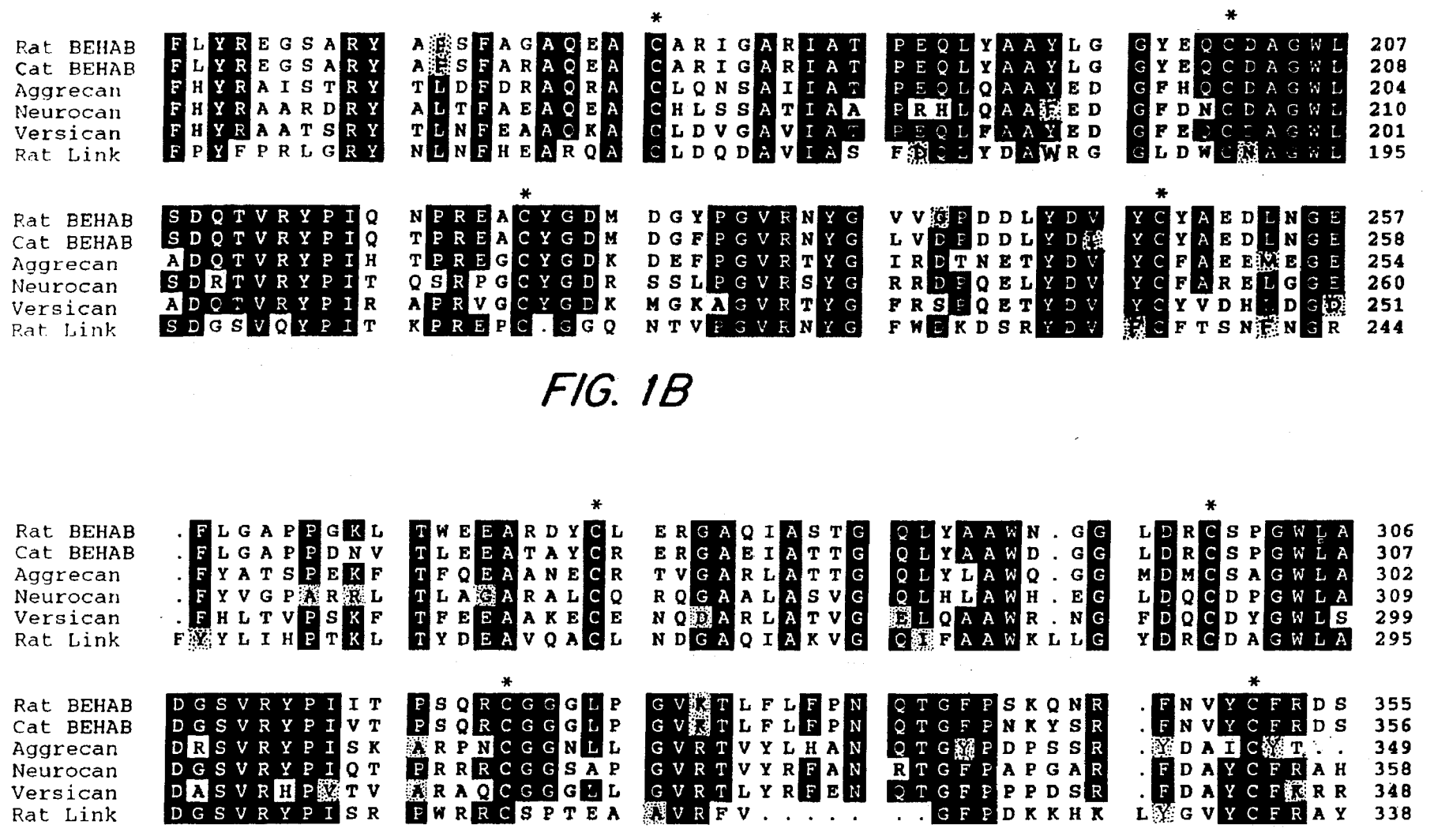

Sequence analyses of rat and cat BEHAB (SEQ ID NOs 8 and 9 and FIG. 1) show a substantial degree of amino acid identity to other members of the PTR family, which includes rat aggrecan, SEQ ID NO 3 (48%); rat neurocan, SEQ ID NO 4 (48%); human versican, SEQ ID NO 5 (46%); and rat link protein, SEQ ID NO 6 (42%). The $NH_2$-terminal domain of this family is defined by two structural motifs, (a) an immunoglobulin (Ig) fold (denoted FIG. 1A) and (b) two PTR folds (PTR1 and PTR2, FIGS. 1B and 1C, respectively). The PTR folds have been suggested to mediate binding to HA. The Ig domain contains two clusters of conserved amino acids around the cysteine residues which generate the disulfide bond of the loop. The consensus sequence YxCxVxH in the COOH-terminal cluster is present in all immunoglobulin and major histocompatability complex proteins, and is also present in BEHAB (FIG. 1). The most conserved region of the PTR family's HA-binding protein domain is the sequence CDAGWL(A/S)D(Q/G)(T/S)VRYPI (SEQ ID NO 11, but using single letter nomenclature defined above) found in PTR1 and PTR2. Two copies of this sequence are also found in BEHAB. The degree of identity of BEHAB between rat and cat is high (84% overall), with the greatest conservation in PTR1. The identity in PTR1 is 95% over the entire domain and 100% over 44 amino acids of the domain. PTR2 shows the next highest homology (86%), followed by the Ig domain (84%). The relative degree of homology between the PTR1, PTR2, and Ig domains observed in rat and cat is also observed between BEHAB and other members of the PTR family. Human human BEHAB is also highly conserved in the PTR1 domain.

This invention provides purified and isolated DNA fragments comprising DNA sequences encoding mammalian brain enriched hyaluronan binding protein, and purified and isolated DNA fragments comprising DNA sequences which hybridize under stringent conditions with sequences encoding the protein. Also provided are RNA sequences corresponding to the DNA sequences.

In one embodiment, the invention provides a purified and isolated DNA fragment derived from rat brain tissue comprising the nucleotides numbered 251 to 1363 of SEQ ID NO 1, and DNA sequences that hybridize under stringent conditions with the sequence. In another embodiment, the invention provides the purified and isolated DNA fragment derived from cat brain tissue comprising the nucleotides numbered 270 to 1403 of SEQ ID NO 2, and DNA sequences that hybridize under stringent conditions with the sequence. In a third embodiment, the invention provides a purified and isolated DNA fragment derived from human brain tissue comprising nucleotides of SEQ ID NO 7, and DNA sequences that hybridize under stringent conditions with the sequence.

Encompassed by this invention are cloned sequences defining BEHAB of this invention, which can then be used to transform or transfect a host cell for protein expression using standard means. Also encompassed by this invention are DNA sequences homologous or closely related to complementary DNA described herein, namely DNA sequences which hybridize to BEHAB cDNA, particularly under stringent conditions that result in pairing only between nucleic acid fragments that have a high frequency of complementary base sequences, and RNA corresponding thereto. In addition to the BEHAB-encoding sequences, DNA encompassed by this invention may contain additional sequences, depending upon vector construction sequences, that facilitate expression of the gene. Also encompassed are sequences encoding synthetic BEHAB proteins exhibiting activity and structure similar to isolated or cloned BEHAB. These are referred to herein as "biological equivalents".

Because of the degeneracy of the genetic code, a variety of codon change combinations can be selected to form DNA that encodes hyaluronan-binding protein of this invention, so that any nucleotide deletion(s), addition(s), or point mutation(s) that result in a DNA encoding the protein are encompassed by this invention. Since certain codons are more efficient for polypeptide expression in certain types of organisms, the selection of gene alterations to yield DNA material that codes for the protein of this invention are preferably those that yield the most efficient expression in the type of organism which is to serve as the host of the recombinant vector. Altered codon selection may also depend upon vector construction considerations.

DNA starting material which is employed to form DNA coding for BEHAB proteins of this invention may be natural, recombinant or synthetic. Thus, DNA starting material isolated from tissue or tissue culture, constructed from oligonucleotides using conventional methods, obtained commercially, or prepared by isolating RNA coding for BEHAB, and using this RNA to synthesize single-stranded cDNA which is used as a template to synthesize the corresponding double stranded DNA, can be employed to prepare DNA of this invention.

DNA encoding the proteins of this invention, or RNA corresponding thereto, are then inserted into a vector, e.g., but not limited to, a p series plasmid such as pBR, pUC, pUB or pET, and the recombinant vector used to transform a microbial host organism. Example host organisms useful in the invention include, but are not limited to, bacterial (e.g., E. coli or B. subtilis), yeast (e.g., S. cerevisiae) or mammalian (e.g., mouse fibroblast or other tumor cell line). This invention thus also provides novel, biologically functional viral and circular plasmid RNA and DNA vectors incorporating RNA and DNA sequences describing BEHAB generated by standard means. Culture of host organisms stably transformed or transfected with such vectors under conditions facilitative of large scale expression of the exogenous, vector-borne DNA or RNA sequences and isolation of the desired polypeptides from the growth medium, cellular lysates, or cellular membrane fractions yields the desired products.

The present invention thus provides for the total and/or partial manufacture of DNA sequences coding for BEHAB, and including such advantageous characteristics as incorporation of codons preferred for expression by selected non-mammalian hosts, provision of sites of cleavage by restriction endonuclease enzymes, and provision of additional initial, terminal or intermediate DNA sequences which facilitate construction of readily expressed vectors. Correspondingly, the present invention provides for manufacture (and development by site specific mutagenesis of cDNA and genomic DNA) of DNA sequences coding for microbial expression of BEHAB analogues which differ from the forms specifically described herein in terms of identity or location of one or more amino acid residues (i.e., deletion analogues containing less than all of the residues specified for the protein, and/or substitution analogues wherein one or more residues are added to a terminal or a medial portion of the polypeptide), and which share the biological properties of BEHAB described herein.

DNA (and RNA) sequences of this invention code for all sequences useful in securing expression in procaryotic or eucaryotic host cells of polypeptide products having at least a part of the primary structural conformation, and one or more of the biological properties of BEHAB which are comprehended by: (a) the DNA sequences encoding BEHAB as described herein, or complementary strands; (b) DNA sequences which hybridize (under hybridization conditions) to DNA sequences defined in (a) or fragments thereof; and (c) DNA sequences which, but for the degeneracy of the genetic code, would hybridize to the DNA sequences defined in (a) and (b) above. Specifically comprehended are genomic DNA sequences encoding allelic variant forms of BEHABs included therein, and sequences encoding RNA, fragments thereof, and analogues wherein RNA or DNA sequences may incorporate codons facilitating transcription or RNA replication of messenger RNA in non-vertebrate hosts.

The invention also provides the BEHAB proteins encoded by the above described DNA and/or RNA, obtained by isolation or recombinant means. In one embodiment, for example, the invention provides a polypeptide having an amino acid sequence depicted in residues numbered 1 to 371 of SEQ ID NO 8 or a biological equivalent thereof. In another embodiment, the invention provides a polypeptide having the amino acid sequence depicted in residues numbered 1 to 378 of SEQ ID NO 9 or a biological equivalent thereof. In a third embodiment, the invention provides a polypeptide set out in SEQ ID NO 7 or a biological equivalent thereof.

Isolation and purification of proteins provided by the invention are by conventional means including, for example, preparative chromatographic separations such as affinity, ion-exchange, exclusion, partition, liquid and/or gas-liquid chromatography; zone, paper, thin layer, cellulose acetate membrane, agar gel, starch gel, and/or acrylamide gel electrophoresis; immunological separations, including those using monoclonal and/or polyclonal antibody preparations; and combinations of these with each other and with other separation techniques such as centrifugation and dialysis, and the like.

It is an advantage of the invention that the isolation and purification of BEHAB provides a polypeptide marker for diagnostic purposes. Since BEHAB is neural-specific, it can be used as a diagnostic agent for brain or other central nervous system tumors or other neuropathological states. Expression of BEHAB is markedly increased in human brain glioma. Thus, this invention provides novel diagnostic methods employing biochemical markers for BEHAB, such as specific and sensitive immunoassays for the detection of BEHAB and patterns of its distribution in samples, to provide not only an indication of ongoing pathological processes in central nervous system tissue, but also differential diagnoses of pathological processes involving specific areas of the central nervous system.

In the practice of the invention, the presence or absence of BEHAB, and/or relative concentrations of BEHAB, are assayed in biological samples obtained from animals or human beings. Typical samples include, but are not limited to, cerebrospinal fluid, serum, urine or tissue homogenates such as those obtained from biopsies. Serum and cerebrospinal fluid are particularly preferred.

For diagnostic purposes, any method may be employed to assay for BEHAB protein. Assay methods include, but are not limited to, Western blots, Northern blots, Northern dot blots, enzyme-linked immunosorbent assays, radioimmunoassays, or mixtures of these.

For example, one embodiment employs an enzyme-linked immunosorbent assay (ELISA). ELISAs typically utilize an enzyme such as horseradish peroxidase, urease, or alkaline phosphatase conjugated to an antibody or conjugated with a tag that interacts with a correspondingly tagged antibody. Example tags, where employed, are avidin and biotin. Test sample is incubated in the wells of microtiter plates with conjugated antibody. If the serum contains BEHAB antigen, the conjugated antibodies adhere to it. Subsequent measurement of enzyme activity estimates how much tagged antibody is present and bound to BEHAB. From that, amounts of BEHAB in the original test sample are calculated. Preferred ELISAs employ substrates known to those skilled in the art to be easily measurable, for example, by viewing color development in comparison with standards or by employing a spectrophotometer. These and other variations on ELISA protocols known by those skilled in the art are encompassed by the invention.

Most preferred substrates are chromophoric or yield chromophoric products, so that enzyme activity can be readily measured by the appearance or disappearance of color. Examples of enzyme substrates include p-nitrophenyl phosphate for alkaline phosphatase, bromocresol purple and urea for urease, p-nitrophenyl-β-galactopyranoside for β-galaactosidase, and the like. Horseradish peroxidase requires hydrogen peroxide in addition to another substrate that serves as a hydrogen donor including, for example, 2,2'-azino-bis-(3-ethylbenzthiazoline-6-sulfonic acid), 5-aminosalicylic acid, o-diaminobenzidine, 3,3'-dimethoxybenzidine, o-phenylenediamine (free base or dihydrochloride), 3,3',5,5'-tetramethylbenzidine (base or dihydrochloride), and the like chromogens.

An alternate embodiment employs a radioimmunoassay (RIA). Typical RIAs employ antigens radiolabelled with $^{125}I$, $^{3}H$ or other isotope that can be easily detected. For example, $^{125}I$-labelled BEHAB can be employed. Antibody is titrated with labelled antigen, and the activity and sensitivity of the antiserum is determined. A dilution series of samples to which known amounts of antigen have been added are distributed in wells of microtiter plates. Antibody is added, the well material and/or the supernatants analyzed for radioactivity after incubation, and compared to a standard curve prepared using pure antigen. Amounts of unlabelled antigen bound are calculated by difference. These and other variations on RIA protocols known by those skilled in the art are encompassed by this invention.

The following examples are presented to further illustrate and explain the present invention and should not be taken as limiting in any regard.

EXAMPLES

Example 1

Rat and cat cDNA clones encoding BEHAB from the two species are prepared in this example.

To isolate rat cDNA clones encoding HA-binding proteins involved in neural development, an unamplified postnatal day 12 rat brain λgt10 cDNA library is screened with rat aggrecan clone pRCP 4 encoding the HA-binding region (described by Doege, K., et al., *J. Biol. Chem.* 262:17757–17767 (1987)). A total of $3.2 \times 10^5$ recombinants are screened resulting in two positives. The library is rescreened with one of these clones, resulting in 15 additional clones. $4 \times 10^4$ phage (per 150 mm plate) are plated with *E. coli* C600 bacteria, immobilized onto nitrocellulose filters, and prepared for hybridization using standard techniques. Filters are prewashed for 1 hour in 1M NaCl, 0.1% sodium dodecyl sulfate (SDS), 20 mM Tris-HCl (pH 8.0) and 1 mMEDTA at 65° C. Filters are then prehybridized for an additional 4 to 6 hours in 50% formamide, 5×SCC (1×SCC=0.15M sodium chloride, 0.015M sodium citrate), 1% SDS, 1×Denhardt's (0.02% Ficoll, 0.02% bovine serum albumin (BSA, Fraction V), 0.02% polyvinylpyrrolidone), 50 mM sodium phosphate (pH 6.7), and 100 µg/ml salmon sperm DNA at 37° C. Hybridization is carried out in the identical solution with the inclusion of $10^6$ cpm pRCP 4 probe/ml for 24 hours at 37° C. For all experiments, radio-labelled probes ($^{32}$P-dCTP, Amersham) are prepared by random priming (Boehringer Mannheim Corp., Indianapolis Ind.) gel purified cDNA inserts, followed by the removal of unincorporated radionucleotides (NICK column, Pharmacia). One post hybridization wash is in 2×SSC, 0.1% SDS and one in 0.2×SSC for 1 hour each are performed at room temperature. Phage DNA is isolated using DE52 (Whatman) and the cDNA insert excised by EcoRI digestion. The insert size of the clones are determined and partial restriction maps are prepared to eliminate redundant clones. The cDNA is gel purified (Gene-Clean®, Bio 101), eight clones subcloned into pBluescript® KS+ (Stratagene, LaJolla, Calif.) and transformed into DH5α (GIBCO BRL, Gaithersburg, Md.).

To isolate cat cDNA clones, random nonamers (1.4 mg) are used to synthesize first cDNA from 5 µg poly A$^+$ RNA isolated from P39 cat cortex, cDNA synthesis is performed according to manufacturer's instructions for the production of nondirectional libraries (Stratagene) and size-fractionated by column chromatography (GIBCO BRL). 50 ng of cDNA is ligated to 1 µg EcoRI cut, phosphatized Lambda Zap® II vector and packaged into phage (Gigapack II Gold®, Stratagene). This yields $0.5 \times 10^6$ recombinants when transfected into XL1-Blue® (Stratagene). The unamplified library is screened with rat clone H1. Hybridization is performed in 6×SSC, 0.1% SDS, 1×Denhardt's and 100 µg/ml salmon sperm DNA at 65° C. Filters are washed twice in 2×SSC, 0.1% SDS and twice in 0.2×SSC at 65° C for 20 minutes. A total of $3.2 \times 10^5$ recombinants are screened, resulting in 5 positives. cDNA inserts of plaque-purified positive clones are isolated in pBluescript® SK$^-$ by in vivo excision.

Example 2

DNA clones prepared in Example 1 are sequenced and compared with previously reported sequences in this Example.

DNA sequencing is performed by the dideoxy chain termination method using Sequenase® (U.S. Biochemical, Cleveland, Ohio). Bluescript SK/KS primers or cDNA specific 20-mers are used. Sequence is verified from overlapping clones or by sequencing both strands of DNA. Sequence compressions are resolved using dITP nucleotides. After labelling, the reactions are incubated at 37° C. for 30 minutes in the presence of 1× reaction buffer, 1 mM dNTPs (pH 7.0) and 0.5 U terminal deoxynucleotidyl transferase to prevent premature termination caused by the use of dITP. Sequence analyses are performed using the University of Wisconsin Genetics Computer Group programs.

For the rat BEHAB sequence, the composite sequence obtained from the overlapping clones identified after subcloning into pBluescript® KS+ as described in the previous Example is used (SEQ ID NO 1; sequence data are recorded in EMBL/GenBank/DDBJ under accession number Z28366). The complete BEHAB coding sequence is 1,113 base pairs. The nucleotide sequence preceding the first AUG contains a consensus sequence for translation initiation. In the 3' untranslated region, only that sequence verified from three clones is presented. The deduced amino acid composition of the BEHAB protein is comprised of 371 amino acids and includes a putative signal peptide cleavage site at Ala-22. The resulting mature protein has a predicted molecular mass of 38,447 kD. Analysis of the deduced amino acid sequence indicates the presence of two NX(S/T) consensus sequences for potential N-glycolsation.

Similarly, the composite cat BEHAB sequence is obtained from the overlapping clones obtained in the pBluescript® SK$^-$ excision as described in the above Example. The results are set out in SEQ ID NO 2 (sequence data are recorded in EMBL/GenBank/DDBJ under accession number Z28367). The complete coding sequence for cat BEHAB is 1,134 base pairs. The first AUG is preceded by both an in-frame termination codon and the translation initiation consensus sequence. The cat BEHAB sequence encodes 378 amino acids which, like the rat, contains a 22 residue signal peptide. However, cat BEHAB contains 6 additional amino acids at the carboxy terminus, resulting in a predicted molecular mass of 38,955 kD. In the cat, Trp-373 is encoded by TGG, while the corresponding rat sequence of TAG results in the termination. This termination sequence is verified in three rat clones and by sequencing both strands of a cat clone. Cat BEHAB also contains one additional site for potential N-glycosylation not present in the rat.

Database analyses at both the nucleic acid and amino acid levels indicate that BEHAB is a previously unreported member of the PTR family of HA-binding proteins. BEHAB has a substantial degree of amino acid identity to the other members of the PTR family, which includes rat aggregan, SEQ ID NO 3 (48%); rat neurocan, SEQ ID NO 4 (48%); human versican, SEQ ID NO 5 (46%); and rat link protein, SEQ ID NO 6 (42%). See FIG. 1. The NH$_2$-terminal domain of this family is defined by two structural motifs, (a) an immunoglobulin (Ig) fold and (b) two PTR folds (PTR1 and PTR2). The PTR folds have been suggested to mediate binding to HA. The Ig domain contains two clusters of conserved amino acids around the cysteine residues which generate the disulfide bond of the loop. The consensus sequence YxCxVxH in the COOH-terminal cluster is present in all immunoglobulin and major histocompatability complex proteins, and is also present in BEHAB (FIG. 1). The most conserved region of the PTR family's HA-binding protein domain is the sequence CDAGWL(A/S)D(Q/G)(T/S)VRYPI found in PTR1 and PTR2. Two copies of this sequence are also found in BEHAB. The degree of identity of BEHAB between rat and cat is high (84% overall), with the greatest conservation in PTR1. The identity in PTR1 is 95% over the entire domain and 100% over 44 amino acids of the domain. PTR2 shows the next highest homology (86%), followed by the Ig domain (84%). The relative degree of homology between the PTR1, PTR2, and Ig domains observed in rat and cat is also observed between BEHAB and other members of the PTR family (Table I and FIG. 1).

TABLE I

Percent Identity of rat BEHAB to Other Members of the PTR Family of HA-Binding Proteins

| Protein | Ig | PTR1 | PTR2 |
| --- | --- | --- | --- |
| Cat BEHAB | 84% | 95% | 86% |
| Aggrecan | 40% | 60% | 51% |
| Neurocan | 37% | 56% | 57% |
| Versican | 36% | 59% | 48% |
| Rat Link | 34% | 48% | 53% |
| CD44 | | 22% | |

Sequence homology is similarly observed for human BEHAB (SEQ ID NO 7). To determine the human BEHAB sequence, total RNA is extracted from a sample of human brain and reverse transcriptase polymerase chain reactions (PCR) performed using degenerate oligonucleotide primers corresponding to the ends of the PTR1 domain in rat and cat. PCR products are subcloned into the TA vector and sequenced by the dideoxy chain termination method described above.

Example 3

In this Example, tissue distribution of BEHAB mRNA is determined by Northern blot analysis and the spatial distribution, by in situ hybridization on central nervous system tissue sections.

For Northern analysis, 25 μg total RNA is denatured in 2.2M formaldehyde, 50% formamide, 1×MOPS (3-(N-morpholino)propanesulfonic acid) buffer at 65° C. for 15 minutes. The RNA is electrophoresed on a 1.0% agarose-formaldehyde gel with 1×MOPS buffer at 50 V with buffer recirculation. The gel is briefly neutralized in transfer buffer (20×SSC) and RNA blotted to Zetaprobe® (BioRad Labs., Hercules Calif.) by capillary transfer. Filters are rinsed briefly in 2×SSC, and RNA is immobilized both by UV cross-linking and baking in vacuuo (80° C. for 1 hour). Hybridization in 7% SDS, 1% BSA, 0.5M phosphate buffer (PB, pH 6.8), 1 mM EDTA and 0.5–2.5×10$^6$ cpm rat H1 probe/ml are carried out for at least 8 hours at 65° C. Filters are washed twice in 5% SDS, 0.5% BSA, 40 mM PB, 1 mM EDTA and twice in 1% SDS, 40 mM PB, 1 mM EDTA at 65° C, and exposed to film (Hyperfilm, Amersham) at −70° C. Molecular sizes are determined relative to RNA molecular weight standards (GIBCO BRL) and 28S and 18S ribosomal RNA observed during UV illumination. The ubiquitously expressed, non-developmentally regulated gene cyclophilin is used to determine equal loading of lanes. Densitometry is performed using the NIH Image program. The two clones recognize the same size mRNA transcript.

Tissue distribution of rat BEHAB mRNA using this procedure shows a single 3.9-kb mRNA transcript detected in adult rat cortex, spinal cord and cerebellum. This transcript is not detected in liver, kidney, spleen, lung or muscle, even with long film exposures. Observed amounts of human BEHAB mRNA is markedly (i.e., at least about four-fold) higher in brain glioma tissue in comparison to what is seen in normal brain tissue using the procedure. Moreover, BEHAB is not detected in non-brain tumor tissues, including breast, lung, or colon tumors.

These observations are confirmed by in situ hybridization to whole embryos, which show that BEHAB expression is restricted to the central nervous system. In situ hybridization is performed on 12 to 14 micron thick frozen sections thaw-mounted onto gelatin-coated slides and postfixed in 0.1M sodium phosphate buffered 4% paraformaldehyde (pH 7.4). Sections are rinsed in 1×PBS (137 mM NaCl, 2.7 mM KCl, 10 mM Na$_2$PO$_4$, 1.8 mM KH$_2$PO$_4$) 2×SSC and acetylated with 0.5% acetic anhydride in 0.1M triethanolamine (pH 8.0). Sections are then rinsed in 2×SSC, 1×PBS, dehydrated in ethanol and delipidated in chloroform. Sections are prehybridized in 2×SSC, 50% formamide at 50° C. for 1 hour, and then hybridized in 0.75 M NaCl, 50% formamide, 1×Denhardt's, 10% dextran sulfate, 30 mM DTT, 10 mM Tris-HCl (pH 7.5), 1 mMEDTA, 100 μg/ml salmon sperm DNA, 0.5 mg/ml yeast tRNA and 10$^6$ cpm probe per slide at 50° C. for 12 to 15 hours. ($^{35}$S)-CTP (New England Nuclear, Boston Mass.) labelled cRNA probes are synthesized using T3 (GIBCO BRL), SP6, and T7 RNA polymerases (New England Biolabs inc., Beverly, Mass.). After hybridization, sections are washed in 2×SSC, 50% formamide, 0.1% BME (β-mercaptoethanol) at 50° C. for 1 hour and treated with 20 μg/ml RNase A in 0.5M NaCl, 10 mM Tris-HCl (pH 8.0) at 37° C. for 30 minutes. Sections are then washed in 2×SSC, 50% formamide, 0.1% BME at 58° C. for 30 minutes and 0.1×SSC, 0.1% BME at 63° C. for 30 minutes and dehydrated. For initial localization of probe, the slides are exposed to film (Hyperfilm, Amersham) for 4 days. Autoradiograms are used as negatives for prints. For higher resolution, the slides are dipped in NTB-2 emulsion (Kodak), developed after 5 days and counterstained with cresyl violet. Neurofilament-middle (NF) antisense and rat clone sense probes are used as positive and negative controls, respectively.

The spatial distribution of BEHAB mRNA within the nervous system is determined at higher resolution by in situ hybridization on tissue sections from P21 rat forebrain, brainstem, spinal cord, and cerebellum. Near adjacent sections are probed with an antisense cRNA probe of a rat clone and positive and negative controls. Using these procedures, BEHAB expression is found to be widely distributed in the brain, in both gray and white matter. The cortex exhibits diffuse hybridization with no laminar specification. Hybridization is detected in white matter tracts, including the corpus callosum, the fimbria of the hippocampus, and the anterior commissure. In the hippocampus, the most intense hybridization is present over neurons; it is highest in the CA1 subfield. The pattern of NF hybridization in the hippocampus is essentially reciprocal to that of BEHAB; the NF probe hybridizes most intensely in subfields CA2, CA3, and in the dentate gyrus. BEHAB hybridization is also seen throughout the inferior colliculus and less intensely in the superior colliculus. In addition to the hippocampus, BEHAB hybridization in gray matter is most intense in the substantia nigra. The rat sense probe generates almost no signal in most of the brain, but a low level of hybridization is seen in the hippocampus and dentate gyrus.

In the brainstem, BEHAB is expressed throughout the reticular formation. Several brainstem nuclei also express BEHAB, including the superior olivary nucleus, the vestibular nuclei, the abducens nucleus and the dorsal column nuclei. A similar hybridization pattern is observed with NF, while no hybridization signal is detected with the sense probe.

BEHAB expression in the spinal cord is greater in the gray matter than in white matter. In the gray matter, BEHAB expression is slightly greater in the ventral than in the dorsal horn. BEHAB hybridization is lacking in the substantia gelatinosa. In the ventral horn, hybridization is seen over motor neurons. In the spinal cord white matter, the size of labelled cells and their distribution indicates that BEHAB is expressed by glial cells. Like BEHAB, NF expression is greater in the ventral horn than in the dorsal horn; however, unlike BEHAB, NF is not detected in the spinal white matter. As observed in the brainstem, no hybridization signal is detected in the spinal cord with the sense probe.

In the cerebellum, BEHAB expression is greatest in the deep cerebellar nuclei. In the cerebellar cortex, labeling is detected in all three cortical layers. In the molecular layer, the distribution of silver grains parallels the distribution of basket and stellate cells. In the Purkinje cell layer, labeling is clustered over Purkinje cells and, in the granule cell layer, it is clustered over Golgi II cells. The white matter of the cerebellar cortex also shows hybridization signal. NF is primarily expressed by Purkinje cells and by cells of the deep cerebellar nuclei. The sense probe generates a low level of diffuse hybridization signal throughout the granule cell layer.

To determine the temporal regulation of BEHAB mRNA expression, Northern blot analysis is performed using total RNA from embryonic and postnatal rat cortex and spinal cord. The non-developmentally regulated gene cyclophilin is used as a control probe to verify equal loading. Unlike actin and tubulin, which exhibit variation of abundance with development, cyclophilin maintains a constant relative abundance throughout the central nervous system with development. The Northern blots are analyzed by densitometry, and band intensity of BEHAB is standardized by calculating a ratio of the abundance of BEHAB to cyclophilin at each developmental age.

In the cortex, BEHAB recognizes a single 3.9-kb mRNA transcript. BEHAB expression is detected at embryonic day 17 and gradually increases to attain adult levels by postnatal day 21. In the spinal cord, BEHAB also recognizes a 3.9-kb mRNA transcript. At all ages except the adult, BEHAB expression is greater in the spinal cord than in the cortex. Like the cortex, BEHAB is present in the spinal cord at embryonic day 17 and gradually increases with age until reaching a maximal level at postnatal day 14. Unlike the cortex, BEHAB expression in the spinal cord then declines slightly.

The expression of BEHAB in the embryo, like in the postnatal animal, is restricted to the central nervous system. BEHAB expression is absent in dorsal root ganglia, a peripheral nervous system structure. Tissues in the embryo that express high levels of closely related genes such as cartilage (which expresses aggrecan) also show no hybridization signal for BEHAB. The distribution of BEHAB expression in the embryonic central nervous system differs slightly from the postnatal brain. The highest levels of BEHAB expression are found in regions that contain mitotically active cells, such as the ventricular zone of the medulla, midbrain, and spinal cord. Expression of BEHAB is heterogenous in the developing brain.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention as defined in the appended claims. The claims are meant to cover the claimed components and steps in any sequence which is effective to meet the objectives there intended, unless the context specifically indicates the contrary.

We claim:

1. An isolated nucleic acid molecule comprising a sequence selected from the group consisting of:

(a) the sequence of a genomic DNA clone or a cDNA encoding a brain-enriched hyaluronan-binding (BEHAB) protein, wherein said DNA or cDNA is isolated from a mammalian brain library, and wherein the noncoding strand of said DNA or cDNA hybridizes under stringent conditions with a DNA probe having the sequence shown as nucleotides 251 to 1363 of SEQ ID NO: 1 or the sequence shown as nucleotides 270 to 1403 of SEQ ID NO: 2;

(b) a sequence degenerate with the sequence of (a); and (c) a sequence complementary to the full length of the nucleic acid of (a) or (b).

2. A nucleic acid molecule according to claim 1 which is DNA.

3. A nucleic acid molecule according to claim 1 which is RNA.

4. A nucleic acid molecule according to claim 1 which encodes a rat BEHAB protein.

5. A nucleic acid molecule according to claim 1 which encodes a cat BEHAB protein.

6. A nucleic acid molecule according to claim 1 which encodes a human BEHAB protein.

7. A nucleic acid molecule according to claim 1 which is a cDNA.

8. A nucleic acid molecule according to claim 1 which is a genomic DNA clone.

9. An expression vector comprising the sequence of a nucleic acid molecule according to claim 1.

10. A host cell transformed or transfected with a nucleic acid according to claim 1.

11. A host cell transformed or transfected with an expression vector according to claim 9.

12. A process for preparing a mammalian BEHAB protein, comprising the steps of:

providing a host cell according to claim 10; and culturing the host cell under conditions suitable for the expression of said nucleic acid.

13. A process for preparing a mammalian BEHAB protein, comprising the steps of:

providing a host cell according to claim 11; and culturing the host cell under conditions suitable for the expression of said nucleic acid.

14. A process according to claim 12, further comprising the step of recovering said BEHAB protein.

15. A process according to claim 13, further comprising the step of recovering said BEHAB protein.

16. An isolated DNA molecule comprising the sequence shown as nucleotides 251 to 1363 of SEQ ID NO: 1.

17. An isolated DNA molecule comprising the sequence shown as nucleotides 270 to 1403 of SEQ ID NO: 2.

18. An isolated DNA molecule comprising the sequence shown as nucleotides 1 to 156 of SEQ ID NO: 7.

19. A vector comprising DNA having the sequence of a DNA molecule according to claim 16.

20. A vector comprising DNA having the sequence of a DNA molecule according to claim 17.

21. A vector comprising DNA having the sequence of a DNA molecule according to claim 18.

22. A host cell transformed or transfected with a vector according to claim 19.

23. A host cell transformed or transfected with a vector according to claim 20.

24. A host cell transformed or transfected with a vector according to claim 21.

* * * * *

UNITED STATES PATENT AND TRADEMARK OFFICE
CERTIFICATE OF CORRECTION

PATENT NO. : 5,635,370
DATED : June 3, 1997
INVENTOR(S) : Susan Hockfield, Diane Jaworski It is certified that error appears in the above-identified patent and that said Letters Patent is hereby corrected as shown below:

Column 1, line 6, insert

-- The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health. --

Signed and Sealed this

Eighth Day of June, 1999

Attest:

Q. TODD DICKINSON

*Attesting Officer*　　　*Acting Commissioner of Patents and Trademarks*